United States Patent
Gaskin et al.

(10) Patent No.: US 9,091,658 B2
(45) Date of Patent: Jul. 28, 2015

(54) PARAMAGNETIC GAS SENSOR APPARATUS AND ADJUSTMENT METHOD

(75) Inventors: Ian C. Gaskin, Tunbridge Wells (GB); Richard P. Kovacich, Crowborough (GB); Christopher R. Edwards, Crowborough (GB); James D. Hobby, Crowborough (GB); Martin Lopez, Rotherfield (GB)

(73) Assignee: Servomex Group Limited (GB)

( * ) Notice: Subject to any disclaimer, the term of this patent is extended or adjusted under 35 U.S.C. 154(b) by 332 days.

(21) Appl. No.: 13/365,814

(22) Filed: Feb. 3, 2012

(65) Prior Publication Data

US 2012/0203529 A1 Aug. 9, 2012

(30) Foreign Application Priority Data

Feb. 8, 2011 (GB) .................................. 1102178.9

(51) Int. Cl.
*G06G 7/57* (2006.01)
*G01N 27/74* (2006.01)

(52) U.S. Cl.
CPC ...................................... *G01N 27/74* (2013.01)

(58) Field of Classification Search
CPC .............................. G01N 27/74; G01N 27/76
See application file for complete search history.

(56) References Cited

U.S. PATENT DOCUMENTS

| 2,416,344 | A | 2/1947 | Pauling |
| 2,666,893 | A | 1/1954 | Munday |
| 3,026,472 | A | 3/1962 | Greene et al. |
| 3,612,991 | A | 10/1971 | Greene |
| 4,794,334 | A * | 12/1988 | Kocache et al. ............... 324/204 |
| 4,807,463 | A | 2/1989 | Ostermeier |
| 4,983,913 | A | 1/1991 | Krause et al. |
| 4,988,946 | A * | 1/1991 | Kocache et al. ............... 324/204 |
| 6,246,227 | B1 | 6/2001 | Hobby et al. |
| 7,102,346 | B2 | 9/2006 | Hobby et al. |
| 2004/0255642 | A1* | 12/2004 | Hobby et al. ................... 73/23.2 |
| 2012/0035882 | A1* | 2/2012 | Stocks et al. ................... 702/150 |

FOREIGN PATENT DOCUMENTS

| EP | 0 379 553 | 6/1989 |
| EP | 0 608 122 | 1/1994 |

(Continued)

OTHER PUBLICATIONS

EPO Search Report dated Jun. 6, 2012, for related EP Application No. 12153176.8, 5 pages.

(Continued)

*Primary Examiner* — Hezron E Williams
*Assistant Examiner* — Mark A Shabman
(74) *Attorney, Agent, or Firm* — Daly, Crowley, Mofford & Durkee, LLP (57) ABSTRACT

This present invention relates to a device for the measurement of the amount of oxygen in a gas mixture, or other gas with significantly different magnetic susceptibility than the background gas mixture, by the use of a suspended test body in a magnetic field that experiences force due to the magnetic susceptibility of the measurand gas. In order to enable a fast time response for the system with a change in oxygen concentration, a flow regime is presented which allows a fast sweep of the measurement volume combined with adjustable, balanced pressure drops via a flow balancing element (or elements) within the flow channels to independently minimise flow related uncertainties.

23 Claims, 7 Drawing Sheets

(56) References Cited

FOREIGN PATENT DOCUMENTS

| | | |
|---|---|---|
| EP | 0 926 490 | 12/1998 |
| GB | 746778 | 3/1956 |
| GB | 2 196 127 | 10/1986 |
| GB | 2465565 A | 5/2010 |
| GB | 2488020 B | 5/2013 |
| WO | WO 89/12821 | 12/1989 |

OTHER PUBLICATIONS

UK IPO combined Search Report and Examination (CSE) report dated Feb. 14, 2012 for related GB Application No. GB1201711.7, 6 pages.
Response to UK IPO combined Search Report and Examination (CSE) dated Jan. 21, 2013 for related GB Application No. GB1201711.7, 10 pages.
UK IPO Examination report dated Jan. 29, 2013 for related GB Application No. GB1201711.7, 2 pages.
G.G. Havens, "The Magnetic Susceptibilty of Nitrogen Dioxide", Phys. Rev. vol. 41, Aug. 1, 1932, pp. 337-344.
Pauling, et al., "An Instrument for Determining the Partial Pressure of Oxygen in a Gas", Contribution from the Research Laboratory, U.S. Steel Corporation, vol. 68, May 1948, pp. 795-798.
Kovacich, et al., "Highly Accurate Measurement of Oxygen Using a Paramagnetic Gas Sensor", Measurement Science and Technology, vol. 17, 2006, pp. 1579-1585.
Search Report from corresponding UK application No. GB1102178.9 dated Apr. 13, 2011, 1 page.
UK Notification of Grant dated Apr. 16, 2013 for GB Application No. 1201711.7, filed Jan. 31, 2012, 2 pages.
International Preliminary Examination Report dated Aug. 14, 2003 for International Application No. PCT/GB02/03558; 6 pages.
International Search Report dated Nov. 29, 2002 for International Application No. PCT/GB02/03558; 3 pages.
European Examination Report dated Feb. 6, 2008 for European Application No. 02 747 607.6; 3 pages.
European Examination Report dated Nov. 12, 2010 for European Application No. 02 747 607.6; 6 pages.
Response to UK IPO office action filed Mar. 28, 2013 for UK Application No. 1201711.7; 27 pages.
Response to EPO office action filed Feb. 7, 2013 for EP Application No. 12153176.8; 13 pages.
European Office Action dated Feb. 6, 2015 for European Application No. 12153176.8; 6 pages.

\* cited by examiner

PARAMAGNETIC GAS SENSOR APPARATUS AND ADJUSTMENT METHOD

CROSS REFERENCE TO RELATED APPLICATIONS

This application claims priority under 35 U.S.C. §119 to United Kingdom patent application No. GB 1102178.9 filed on Feb. 8, 2011, which is incorporated herein by reference.

FIELD OF INVENTION

This present invention relates to apparatus for the measurement of the amount of oxygen in a gas mixture, or other gas with significantly different magnetic susceptibility than the background gas mixture, by the use of a suspended test body in a magnetic field that experiences force due to the magnetic susceptibility of the measurand gas.

BACKGROUND

The measurement of oxygen gas by its paramagnetic property is a well established technique which is approved for many industrial and medical applications, where it generally provides excellent selectivity, accuracy and reliability. This is because oxygen is one of the few gases which exhibit paramagnetism, meaning it will be strongly attracted by a magnetic field. Most other common gases are diamagnetic, which is a very much weaker magnetic effect.

The force Fm that acts on a spherical test body in an inhomogeneous magnetic field is proportional to its volume V, the magnetic field gradient HdH/dz and the volume magnetic susceptibility difference between the test body X1 and surrounding sample gas X2 (see "The magnetic susceptibility of nitrogen dioxide", G G Havens, Phys. Rev. vol 41 (1932) pp. 337-344). That is:

$$Fm \propto V*H*dH/dz*(X1-X2)$$

Since the volume magnetic susceptibility of the sample gas is proportional to the sample gas density, the force is proportional to the partial pressure of oxygen. The volume magnetic susceptibility of oxygen at room temperature is $1.9 \times 10^{-6}$ SI units, whereas nitrogen (a typical background gas) is $-6.7 \times 10^{-9}$ SI units. Therefore the force due to oxygen in the gas mixture, even small amounts, is substantially larger than other gas components, hence the excellent selectivity of this measurement principle to oxygen.

The force itself is quite weak, typically a few micro-Newtons with pure oxygen for magnetic field strengths and test body volumes that can be practically achieved. Consequently a very sensitive system is required to measure this force with the necessary resolution required for oxygen sensing applications.

The typically preferred arrangement uses a magnetic susceptibility torsion balance inside a sealed cell which is arranged to admit the sample gas. The torsion balance comprises a test body having a particular shape, and filled with a diamagnetic gas such as nitrogen. The body is suspended in a non-uniform magnetic field in the sealed cell, and is typically balanced by initially filling the cell with nitrogen. When the cell is subsequently filled with a test gas containing oxygen, the paramagnetic oxygen gas is attracted to the stronger part of the magnetic field, and the test body rotates. This rotation is detected and used to indicate the oxygen content of the sample gas.

Such a device was first described by Havens (see reference above) who carefully studied the factors that govern sensitivity of the test body, in particular its shape, finding that a sphere is optimum. Other magnetic susceptibility torsion balances using different test bodies have been examined as early as 1850 (Faraday M (1851), Proc. R. Inst., vol. 1, p. 229). However, they did not match the sensitivity achieved by Havens.

The first commercial oxygen analyser using a magnetic susceptibility torsion balance was developed by Pauling, Wood and Sturdivant under US government contract NDCrc-38 (J. Am. Chem. Soc. 68 (1946), 795) and is disclosed in U.S. Pat. No. 2,416,344 (application filed 23 Aug. 1941). The test body consists of a pair of identical hollow glass spheres on either end of a rigid bar that is suspended by a fine glass fibre under tension, which provides a very soft torsion spring constant. The spheres are made as light as possible so the inertia is not much larger than the magnetic force, and balancing weights are also added to minimise the effect of orientation sensitivity. This assembly is placed between magnet poles that generate a strong magnetic field gradient and arranged so the force acting on both spheres reinforces the torque.

Movement of the test body is detected using an optical lever. This consists of a light source that makes a beam of light which reflects off a mirror at the centre of the test body and then onto an optical readout, which indicates displacement of the subtended beam. The beam displacement at the optical readout is proportional to the angular movement of the test body and the length of the optical lever arm, i.e. the distance between the mirror and the readout. Therefore good angular resolution may be obtained by increasing the optical lever arm length as necessary while maintaining focus of the beam spot on the readout.

The optical lever is also advantageous for rejecting errors due to rectilinear motion and vibration, as the angular movement is detected from the centre of a balanced test body that is only allowed to rotate about its principal axis.

Later inventions made significant improvements to the manufacturability and performance of magnetic susceptibility torsion balances, in particular through the use of an electronic optical lever to detect and control motion of the test body using a feedback system. Munday in GB 746,778 discloses an optical lever feedback system in which a photo-electric cell is used as the optical readout and a wire coil, attached around the test body that conducts via the suspending wire, is used to provide feedback. The system keeps the test body at a null position by reacting to motion of the test body. By maintaining the test body substantially in the same position in this way, all measurements can be recorded at the position of maximum sensitivity. This is achieved by amplifying the photo-electric cell signal to generate a current in the wire coil that produces a magnetic torque equal and opposite to the perturbing force that would otherwise push the test body away from its null position, i.e. the magnetic force due to a change of the amount of oxygen in the sample gas. This current can then be measured in order to determine the magnetic force, and hence the oxygen content of the sample gas. A similar system is disclosed by U.S. Pat. No. 3,026,472, but feedback is provided by electrostatic actuation of the test body.

Many modern oxygen sensors still use the optical lever with refinements. For example, "Highly accurate measurement of oxygen using a paramagnetic gas sensor", R P Kovacich, N A Martin, M G Clift, C Stocks, I Gaskin, J Hobby, Measurement Science and Technology, vol 17 (2006), pp. 1579-1585) describes an optical lever with a solid state source (light emitting diode) in place of an incandescent one and a pair of photo-diodes connected in reverse polarity to provide a zero voltage null position when both photo-diodes are equally illuminated, i.e. when the beam spot centre is exactly in between the photo-diodes. Using a pair of photo-diodes also has the advantage of rejecting common mode errors, such as intensity fluctuations of the light source. This electronic optical lever feedback system gives much improved sensitivity, linearity and stability.

Several inventions have tried using arrangements without the optical lever, such as an electrostatic sensing and actuation system as disclosed in U.S. Pat. No. 3,612,991 and an oscillating magneto-dynamic system as disclosed in U.S. Pat. No. 6,246,227. However, both have disadvantages. The electrostatic system requires gold plating of the test body which makes manufacture difficult, requires high voltages (up to 100 Volts) thus limiting compact electronic design, and is not as corrosion resistant as other metals such as platinum. Most plating metals are not suitable as they tend to be paramagnetic or prone to corrosion. The oscillating system is disadvantaged by cross sensitivity to gases with a significantly different viscosity to molecular weight ratio, such as helium and halocarbons with heavy molecular weight; gases which are used as anaesthetic agents.

A diffusion based device can be designed to give a high precision oxygen measurement (typically <0.2% Oxygen or better accuracy) with low sample flow rate dependence. However, certain applications, such as those in medical anaesthesia or pulmonary function testing, require a fast response to any change in the oxygen concentration level. This in turn requires a fast sweep of the gas volume in the vicinity of the nitrogen filled spheres and hence a direct flow of gas through the measurement cell and a minimisation of internal volume. However, any such motion of the gas will have a momentum impact on the spheres and this can appear as noise on the signal due to induced oscillatory forces and potentially a signal bias unless the system is perfectly symmetric with respect to gas flow regime and sphere morphology and construction. In short, there can be a strong dependence of signal with flow rate as the price to pay for a fast time response—they are coupled parameters and cannot easily be minimised simultaneously.

Figure 1:
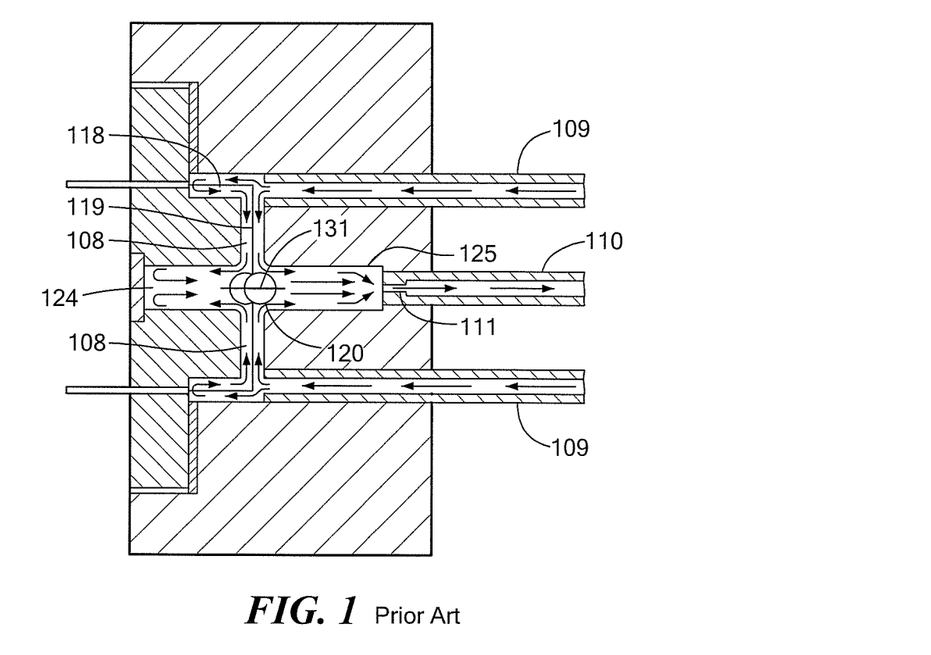
FIG. 1 represents a first example sensor apparatus, as is known in the art.

In an effort to reduce the dependence of signal with flow rate for devices with fast response times, previous designs such as U.S. Pat. Nos. 4,988,946 and 7,102,346 have attempted to reduce as much as possible all asymmetry in the flow path and tried to shield the test body from direct or large magnitude velocity vectors by controlling the incoming gas direction and type of flow past the suspension test body. However, the internal asymmetry can never be reduced to zero due to normal manufacturing tolerances and essential asymmetrical features such as magnets, test body and mounting. Similarly, the flow past the test body can never be reduced to zero as the gas must flow through the device. This prior art will now be discussed in more detail, although the magnetic fields and optical feedback systems used in the measurements will not be discussed here—only the design of the gas flow regime within the devices to reduce the asymmetry and flow momentum impact on the test body. FIG. 1 shows a cross-section through an apparatus that is shown and described in U.S. Pat. No. 4,988,946, in order to illustrate the gas flow regime. In this case, the test body (120) consists of a dumb-bell arrangement with hollow glass spheres filled with nitrogen, a mirror, a feedback coil and a suspension strip. The incoming gas enters via twin inlet pipes (109) used in a symmetrical configuration so as to sweep the measurement chamber and also to reduce disturbance of the test body (120) by virtue of halving the speed of gas impinging on the dumbbell (131) and attempting to equalise it by the simultaneous arrival from both sides. The inlet pipes are also positioned so as to admit the gas directly aimed at the spring (118) to which the suspension strip (119) is welded and which is situated in a very small space. The incoming gas turns and runs along the channel (108) which houses the suspension strip (119). Upon arrival to the middle part of the chamber, the gas turns towards the outlet pipe (110) and emerges out of the chamber. The outlet includes a restrictor (111) which is chosen so as to stop the immediate turning of the gas to the outlet from its emergence from the channels (108) (which would leave the gas in the front of the mid-chamber (124) to exchange by diffusion, which is slow). When the restrictor is chosen correctly, the pressure built up in the rear part of the mid-chamber (125) ensures that part of the gas turns towards the front part (124) and sweeps it and thus a fast response time is achieved.

Figure 2:
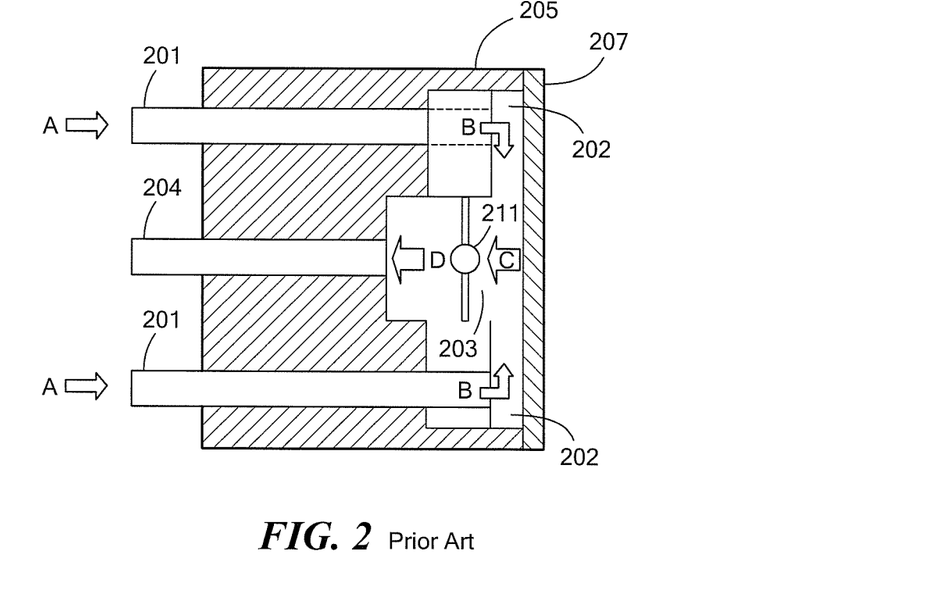
FIG. 2 represents a second example sensor apparatus, as is known in the art.
Figure 3:
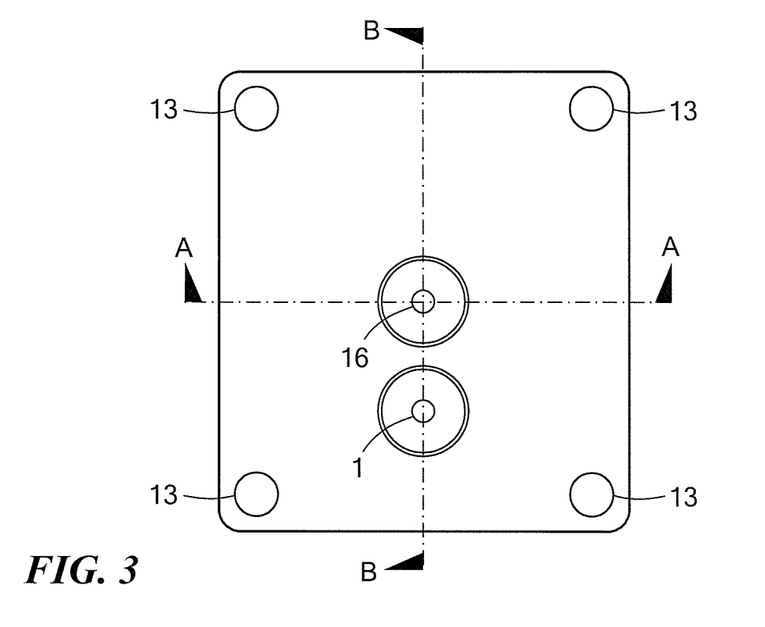
FIG. 3 shows the top view of a manifold according to a preferred embodiment.
Figure 4:
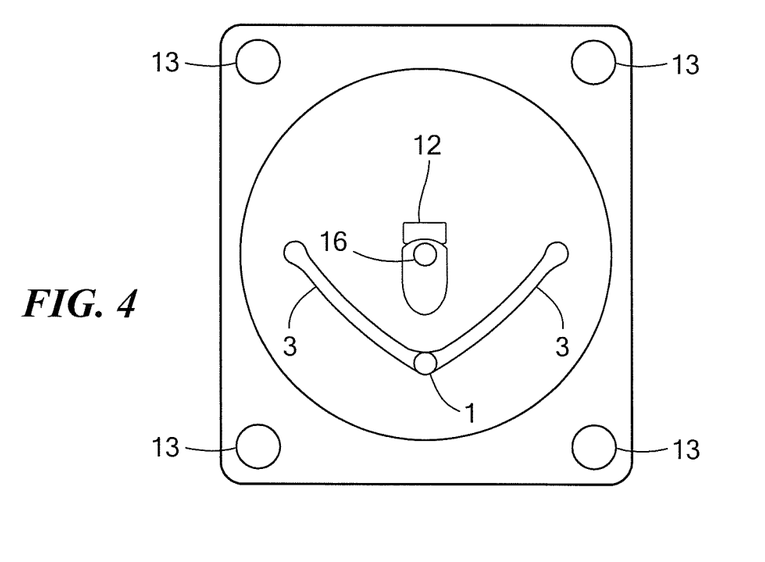
FIG. 4 shows the underside of the manifold of FIG. 3.
Figure 5:
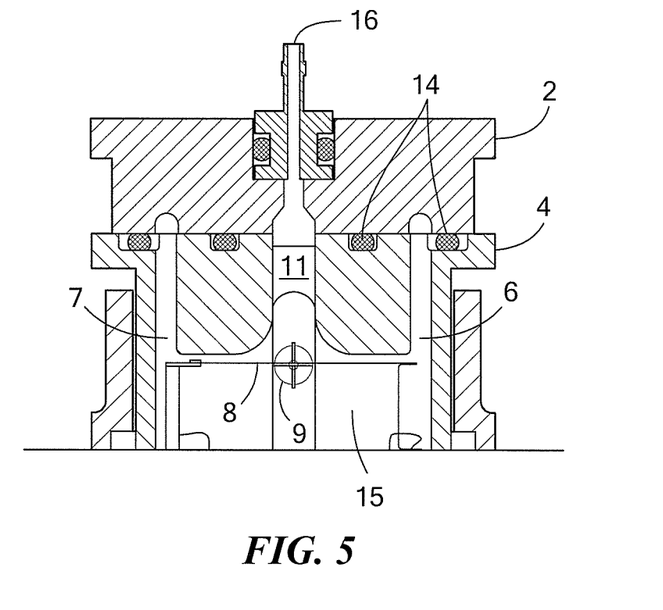
FIG. 5 shows a cross section through an apparatus according to the preferred embodiment, taken along the line A-A in FIG. 3.
Figure 6:
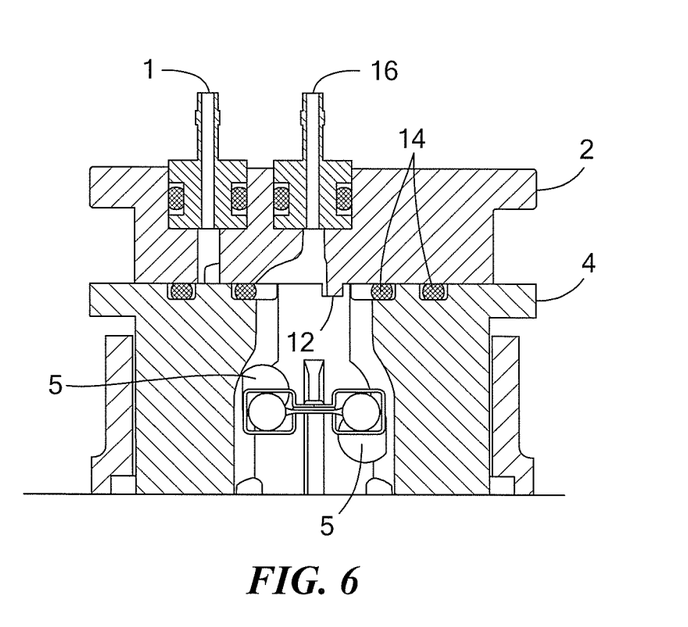
FIG. 6 shows a cross-section through an apparatus according to the preferred embodiment taken along the line B-B in FIG. 3.
Figure 7:
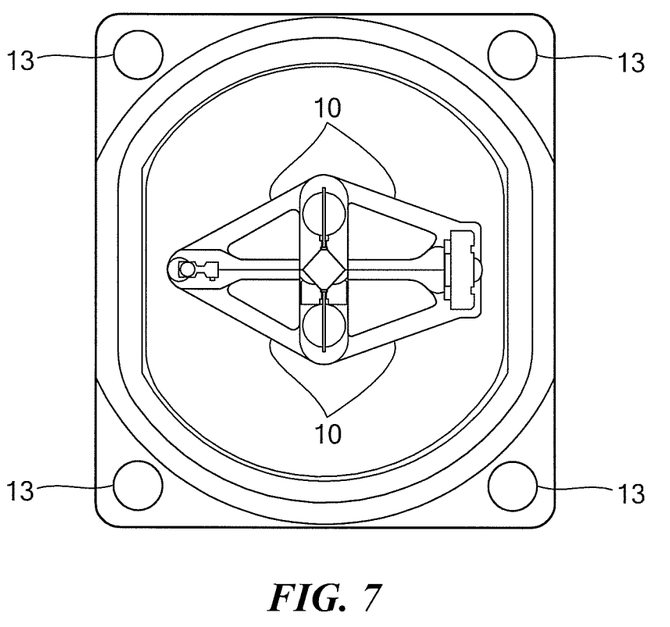
FIG. 7 shows the underside of the main header of the preferred embodiment.

FIG. 2 shows a cross section through an apparatus that is shown and described in U.S. Pat. No. 7,102,346, in order to illustrate the flow regime. The test body is a similar arrangement to that in FIG. 1. The gas sample enters via ports (201) (arrows A). The inlet ports are of narrow diameter to reduce any smearing of concentration changes in the gas flow. At the front of the device, the gas is forced to undergo a ninety degree turn (arrows B) to enter a narrow channel (202) defined between the body (205) and the face plate (207). This in turn breaks up the gas flow and causes the flow channel (202) to have a wide distribution of momentum and to consist of very small vortices. The gas enters the measuring chamber (203), where the large increase in cross section causes the flow per unit area to fall significantly. The test body (211) is mounted as shown such that it lies parallel to and in symmetrical relation to the narrow channel (202). The gas then flows past the test body (211) (arrows C). Due to these fine vortices within the flow and the symmetrical flow across either side of the test body, the net force on the test body is small and hence the influence of any change in flow rate is lower than would be otherwise. Furthermore, as the measurement chamber is actually being swept by the gas flow, any change in sample concentration occurs rapidly compared to diffusion. After passing through the measurement chamber, the gas enters the exhaust port (204) (arrow D) accelerating the gas flow. The exhaust port is preferentially of larger diameter than the inlet ports to permit any chaotic flow to be rapidly expelled. An extended gap at the back of the chamber compared to the front also reduces the effect of any turbulence generated as the sample enters the smaller outlet bore. The overall effect is that a fast time response with acceptable flow error is achieved.

SUMMARY OF INVENTION

A first aspect of the invention provides a paramagnetic gas sensor apparatus, comprising: a body defining a chamber with gas inlet means and at least one gas outlet for allowing gas flow through the chamber; means for creating a magnetic field within the chamber in a first direction; a test body; means for mounting the test body in said chamber for rotation about an axis parallel to the direction of the magnetic field in response to a torque applied to the test body in dependence on the magnetic susceptibility of a measurand gas; characterised in that the gas inlet means is arranged to supply gas to the chamber from positions at opposite sides of the chamber and in opposed directions, and at least one flow balance element is present to provide an asymmetry in the gas flow pathway.

In one embodiment, the flow balance element comprises at least one protrusion extending into the fluid flow path to restrict the fluid flow path, but other flow-adjusting elements may be provided such as one or more indentations, or combinations of protrusions and indentations. The position of a particular flow balance element may be determined via computer modelling techniques or by monitoring the effects of a gas flow for different positions of the flow balance element. Computer modelling techniques or monitoring can also be used to select a size or format of the flow balance element.

The at least one flow balance element can be arranged to correct or mitigate a pressure imbalance in the vicinity of the test body and/or to correct or mitigate any flow-generated net torque on the test body due to the residual inherent asymmetry of the apparatus. The presence of the flow balance element achieves a reduction in flow dependence compared to an identical device without a flow balance element. The gas inlet means are arranged to supply gas to the chamber from at least two positions at opposite sides of the chamber. Gas flow from each of the positions will preferably be parallel to the direction of the magnetic field but flowing in opposed directions in order to minimise errors resulting from gas flow upon the test body.

The apparatus according to this aspect of the invention differs from prior art in that a flow balancing element (or elements) is used in order to balance the pressure drops across the test body from the differing flow paths around the test body. The inventors of the present invention have determined that an unbalanced fluid flow or pressure imbalance can be problematic, even after all practical measures have been taken to ensure that the internal volume of the device is essentially symmetrical and that the test body is suitably shielded from flow momentum impact. This flow balancing element (or elements) allows tuning of the system to minimise net flow effects on the suspension test body and also allows the use of flow paths around the test body (e.g. around each of two glass spheres filled with diamagnetic gas) that are only similar rather than absolutely identical symmetrical flow paths. This has advantages of improved flow error performance due to limitations of manufacturing tolerances or even allows deliberate design of asymmetrical geometry and reduced shielding of the test body, whether for cost reduction, for mechanically advantageous reasons or for any other reasons, to be implemented without detracting from the flow performance. For instance, a more aggressive flow regime can be pursued incorporating features such as bypass channels to improve flushing of the internal volume. Since the pressure drops in the flow regime in the vicinity of the test body are balanced by the flow balance element, there is a very effective net cancellation of any flow induced uncertainties. This is in marked contrast to the prior art where only symmetry and/or flow shielding can be used to reduce flow error, limiting their design.

Because prior art devices have a finite, non-zero flow dependence at any given flow speed, then increasing the flow speed to reduce response time must increase flow error, in other words, response time and flow error are coupled and cannot be minimised simultaneously. The performance of the flow balance element can be controlled by varying its position, number, size, shape and surface finish In one embodiment, a flow regime is provided which allows a fast sweep of the measurement volume combined with adjustable, balanced pressure drops across the flow channels using a flow balance element to minimise flow-related pressure imbalances. This enables a fast time response for the system with a change in oxygen concentration with low dependence on flow and the two parameters are now de-coupled and can be minimised simultaneously.

One embodiment includes a magnetic susceptibility torsion balance inside a sealed cell that is arranged to admit a sample gas. The torsion balance comprises a test body (for example with two glass spheres filled with a diamagnetic gas such as nitrogen) suspended in a non-uniform magnetic field in the sealed cell. Such torsion balances are typically calibrated by using two gases of known paramagnetic susceptibility, for example, nitrogen and a known concentration of oxygen in nitrogen mixture. When the cell is subsequently filled with a test gas containing oxygen or other paramagnetic gas, the paramagnetic gas is attracted to the stronger part of the magnetic field, and the test body rotates. An optical lever feedback system with photo-detectors, or other suitable means, is used to detect this rotation and a wire coil, attached around the test body that conducts via the suspending wire, is used to provide feedback. The system keeps the test body at a null position by reacting to motion of the test body. By maintaining the test body substantially in the same position in this way, all measurements can be recorded at the position of maximum sensitivity. This is achieved by amplifying the photo-electric cell signal to generate a current in the wire coil that produces a magnetic torque equal and opposite to the perturbing force that would otherwise push the test body away from its null position, i.e. the magnetic force due to a change of the amount of oxygen in the sample gas. This current can then be measured in order to determine the magnetic force, and hence the paramagnetic gas content of the sample gas.

One embodiment of the apparatus includes means for determining the presence of a first asymmetry in the gas flow pathway, and means for adjusting the at least one flow balance element. A control mechanism is provided in one embodiment, which is responsive to detection of a net torque on the test body caused by a gas flow, to reduce the net torque Another aspect of the invention provides a method for adjusting a flow path within a paramagnetic gas sensor apparatus comprising:
  determining the presence of a first asymmetry in a gas flow pathway within the apparatus; and
  in response to the determination of the first asymmetry, providing at least one flow balance element in the gas flow pathway to create a second asymmetry.

In one embodiment, the above-described method for adjusting a flow path within a paramagnetic gas sensor apparatus is applicable to an apparatus comprising a body defining a chamber with gas inlet means and at least one gas outlet, to define at least one gas flow pathway for allowing gas flow through the chamber, means for creating a magnetic field within the chamber in a first direction, a test body, means for mounting the test body in said chamber for rotation about an axis parallel to the direction of the magnetic field in response to a torque applied to the test body in dependence on the magnetic susceptibility of a measurand gas.

The presence of the first asymmetry may be determined by monitoring the effect of a gas flow through the flow path, such as detecting the effects of the gas flow's momentum on a test body of the paramagnetic gas sensor. Where the momentum of the gas generates a net torque on the test body, it indicates an asymmetry. The arrangement of the at least one flow balance element can be chosen to reduce or minimize flow-dependent imbalances, such as to minimize the effect of the momentum of the gas flow on the test body. For example, the position, size, number, shape and/or surface finish of the elements can be chosen to mitigate an unbalanced flow. The effect of the at least one flow balance element on the gas flow can be monitored, to identify an arrangement of the at least one flow balance element at which the net torque is reduced or cancelled. This creation and adjustment of an asymmetry to balance the effect on fluid flow of a first asymmetry can be carried out for different gases and flow rates.

In one embodiment of the invention, arranging the at least one flow balance element comprises modelling, in a computer system, the effects on gas flow of adjusting one or more of the position, size, number or format of one or more flow balance elements for one or more gas flow rates; determining an optimum flow balance element arrangement; and arranging the at least one flow balance element in the optimum arrangement.

BRIEF DESCRIPTION OF DRAWINGS

Embodiments of the invention are described below in more detail, by way of example, with reference to the accompanying drawings in which.

DETAILED DESCRIPTION OF PREFERRED EMBODIMENTS

Various features of an apparatus according to a preferred embodiment of the invention are illustrated in FIGS. 3-7, although equivalent design benefits could also be obtained for differing requirements such as absolute flow rates, containing the same essential elements. The test body in this embodiment is similar to that described in prior art. Various alternative embodiments are mentioned below.

The gas enters via the inlet gas port (1) in the manifold section (2) and is split internally into two flow channels (3) of equal dimensions. The internal split means that the balance of flow can be controlled via the part dimensions and manufacture rather than by the end user or external plumbing of the device, which may unintentionally cause an extra flow imbalance. However, this split can be implemented external to the device in an alternative embodiment. The gas then passes from the manifold section into the main header (4) which surrounds the paramagnetic suspension assembly. The header contains the magnets (5) and a 'cruciform' shaped void with one channel containing the suspending wire and another channel at right angles containing the test body. The void is designed to encompass the suspended test body assembly with minimal clearance required for assembly and free movement of the test body, thus in general, minimising the internal volume of the gas sample space. The flow enters the first channel containing the suspending wire via two ports, one above the spring (6) and one above the fixed post (7). These are at either end of the channel containing the suspending wire (8). Each flow stream must then turn ninety degrees and move along this channel towards its centre where the second channel containing the test body (9) is situated, where they converge. The flow, now largely recombined, then turns another ninety degrees and moves through the second channel containing the test body, thus sweeping it. At the point that the two channels meet, large radii are used to reduce flow separation by utilising the Coanda effect. This aids the turning of the flow into the second channel and reduces turbulence and momentum impact around and on the mirror and spheres of the test body. The flow from the first channel enters the channel containing the test body at its centre and mainly turns to flow at right angles to the test body. To effectively sweep the ends of the channel containing the test body, bypass channels (10), that lead from each end of the channel containing the suspending wire, provide energy to the flow in these regions which would otherwise be stagnant, thus improving sweeping efficiency and hence reducing response time. The flow then moves towards the exit aperture (11) of the header. In this preferred embodiment, the exit aperture is large enough to view the spheres through to facilitate accurate and repeatable assembly, but other embodiments could be used with a different aperture size. The exit aperture of the header leads back into the manifold section where the flow exits in a direction opposite to the original inlet.

The manifold section contains an off-centre flow balancing element (12), near the exit aperture of the main header, used to control the flow sensitivity. This works by rectifying any pressure differential across the spheres. In this embodiment, the pressure differential is originally generated by the inherent asymmetry of the magnet recess geometry and any asymmetry caused by the mechanical limitations of the manufacturing and assembly methods of the device that cannot be reduced any further by any practical means. For any particular shape, the extent to which the flow balance element alters the flow sensitivity may be governed by its "height", i.e. the amount it protrudes upstream into the flow from the exit, although other embodiments could equally tune the pressure differential via changes in surface area, shape, surface roughness or other flow balance element properties, format and/or location. The manifold section also contains features for mounting the device (13). Between the manifold section and main header there are elastomeric seals (14) that separate the inlet and outlet flows from each other and from the external atmosphere. For mass production, both manifold section and main header can be injection moulded polymer parts.

Figure 8:
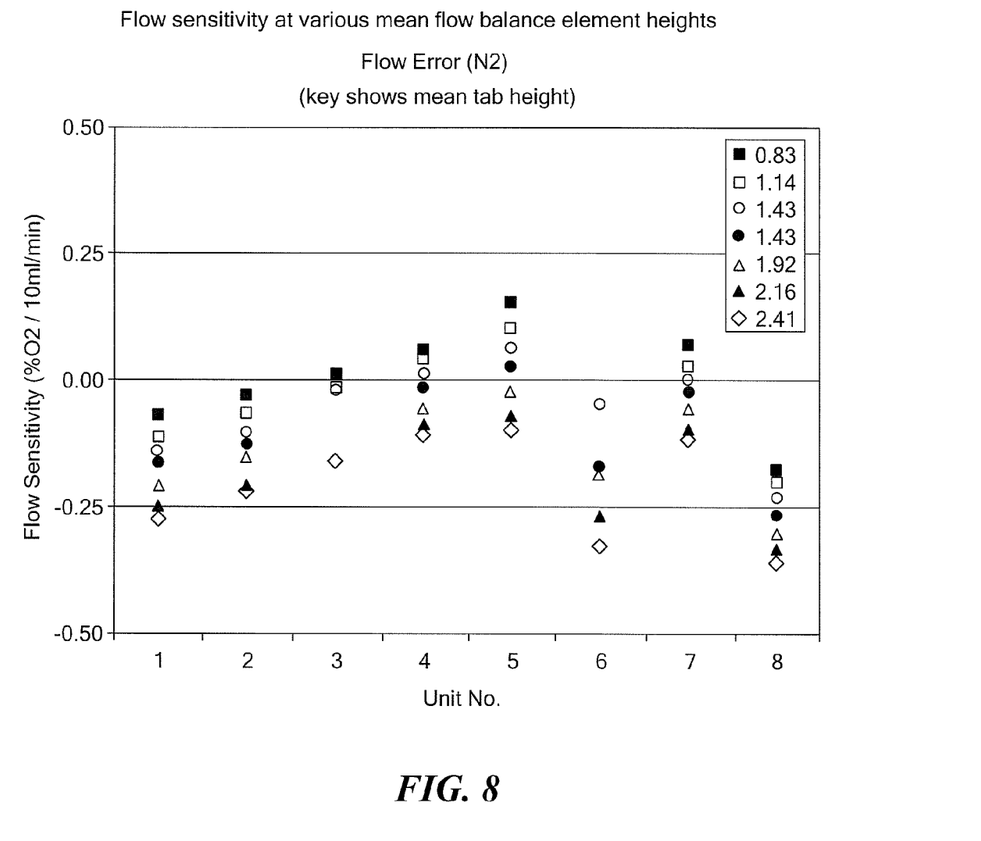
FIG. 8 shows flow sensitivity at various mean flow balance element heights for the preferred embodiment.

The results for the measurement uncertainties caused by the flow effect are illustrated in FIG. 8 for 8 preferred embodiment prototype devices which show that, in general, as the flow balance element height is reduced, the flow uncertainty becomes more positive for any given device. However, it can also be seen that the absolute value of flow uncertainty is not solely determined by the flow balance element dimension. The spread of results is likely to come from variation in the test body and other parts of the assembly. The standard deviation in flow uncertainty, and the relative flow uncertainty of one device to the others, remained fairly constant, whilst the standard deviation in flow balance element height, and the relative flow balance element height of one device to the others changed throughout the tests.

Figure 9:
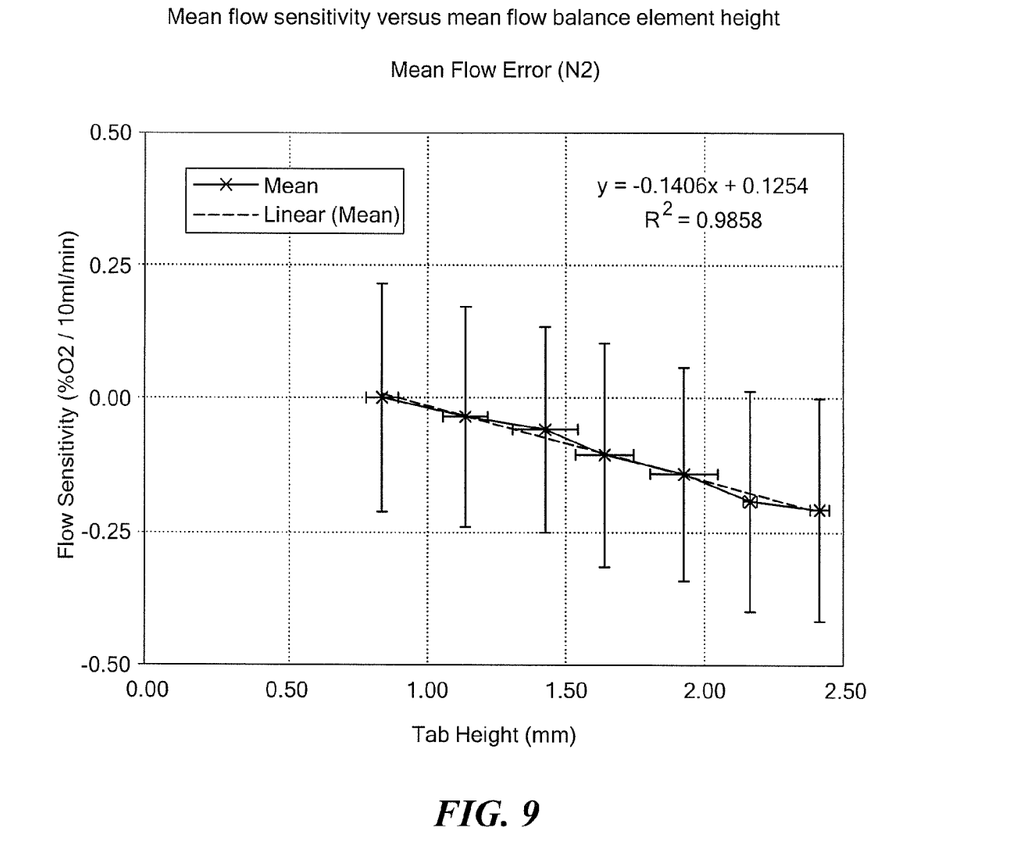
FIG. 9 shows mean flow sensitivity versus mean flow balance element height for the preferred embodiment.

In this particular case, the target specification for flow uncertainty was $<\pm 0.25\%$ $O_2$ for a $\pm 10$ ml/min change in the range 50 to 250 ml/min. FIG. 9 shows the mean data points with uncertainty bars representing $\pm 2$ standard deviations (approx 95.5%) in both flow error and flow balance element height. Using a linear fit shows that the dependence of flow error on flow balance element height is approximately $-0.14\%$ $O_2/10$ ml/min per mm, and that, for the devices tested, a mean flow uncertainty of zero is obtained with a flow balance element height of approximately 0.9 mm. The gradient is such that general manufacturing tolerances on flow balance element height ($\pm 0.1$ mm) should not cause the flow uncertainty to exceed the specification. The specification represents about 2.4 standard deviations (approximately 98.4%). Note that if required, an adjustable flow balance element could be used to optimise each individual device for flow uncertainties.

Figure 10:
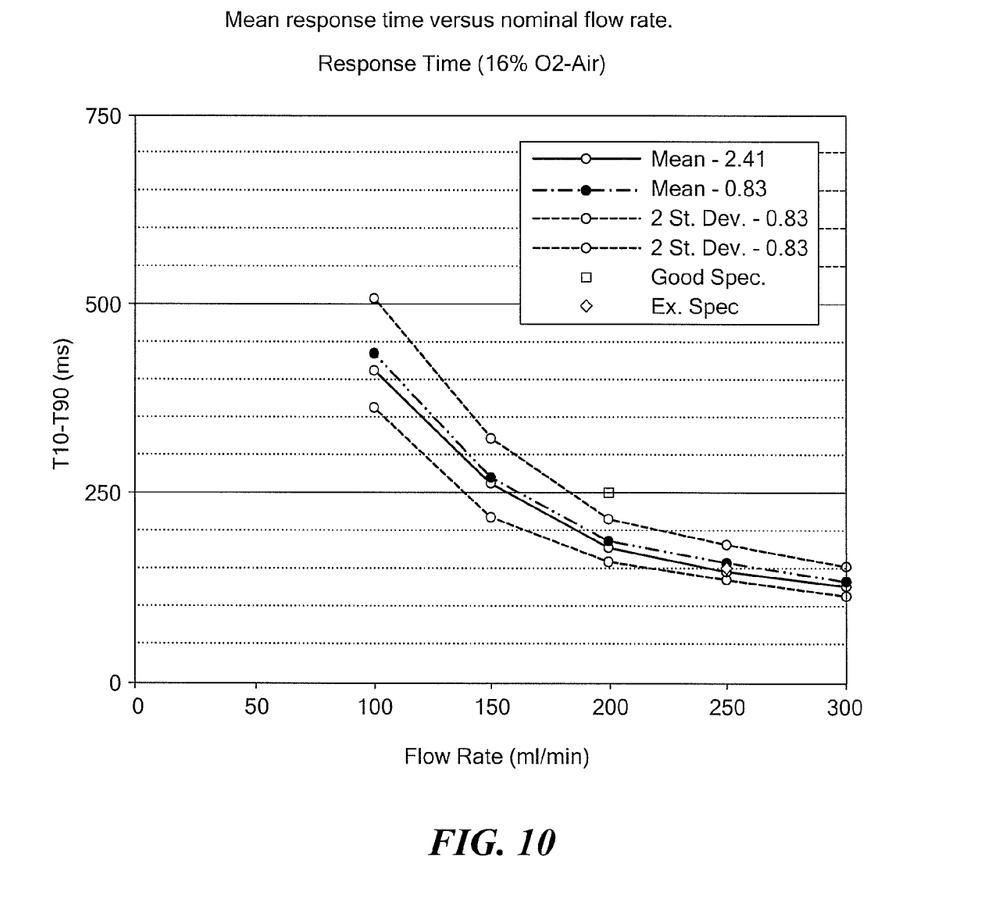
FIG. 10 shows mean response time versus nominal flow rate for the preferred embodiment.

The response times were first obtained with the tab height at 2.41 mm mean, and then again once optimised for flow uncertainty (0.83 mm mean) to establish the effect of flow balance element height on response time. FIG. 10 shows the mean response times for all devices at each flow rate. The 2 solid lines show the difference between mean tab heights of 2.41 and 0.83 mm. The dashed lines show ±2 standard deviations at each flow rate for the optimised version (0.83 mm mean). It can be seen that the effect of flow balance element height on response time is minimal (approx. 6.3 ms per mm @ 200 ml/min) and that the devices easily meet the minimum specification of 250 ms @ 200 ml/min. In this case, assuming the tested devices are representative of the total population, the flow balance element height would be set at 0.8-0.9 mm to minimise the average impact of flow, whilst maintaining a fast flow response.

The flow balance element has been illustrated for the preferred embodiment, however, the flow balance element may be situated either upstream or downstream from the test body or indeed may consist of a plurality of flow balance elements, upstream and/or downstream. The shape may be of different formats depending on the required performance, but may range from a bluff body to a stream-lined raised or indented section. The material and surface finish characteristics of the flow balance element is also of importance, for example, a roughened surface may induce more turbulence and increased backpressure compared to a smooth surface with the same physical size and shape. The format and location of the flow balance element may also be adjustable to allow individual device optimisation of the flow error.

The invention claimed is:

1. A paramagnetic gas sensor apparatus, comprising:
a body defining a chamber with at least one gas inlet and at least one gas outlet defining at least one gas flow pathway for allowing gas flow through the chamber; the at least one gas flow pathway having a first asymmetry that creates a first region of asymmetrical fluid flow;
a set of magnets for creating a magnetic field within the chamber in a first direction;
a test body; and
a torsion balance for mounting the test body in said chamber, for rotation about an axis parallel to the direction of the magnetic field in response to a torque applied to the test body, which torque is generated in dependence on the magnetic susceptibility of a measurand gas;
wherein the at least one gas inlet is arranged to supply gas to the chamber from positions at opposite sides of the chamber and in opposed directions, and at least one flow balance element provides a flow-modifying asymmetry in a gas flow pathway that creates a second region of asymmetrical fluid flow to mitigate a pressure imbalance in the vicinity of the test body that is caused by the first asymmetry.

2. The apparatus according to claim 1, wherein the gas inlet is arranged to supply gas to the chamber in directions parallel to the direction of the magnetic field.

3. The apparatus according to claim 1, wherein the torsion balance is operative to maintain the test body in a null position.

4. The apparatus according to claim 1, further comprising a signal generator to give an indication of the paramagnetic susceptibility of the gas.

5. The apparatus according to claim. 1, wherein the flow balance element is adjustable.

6. The apparatus according to claim 5, wherein the flow balance element is in a fixed location and with an adjustable format.

7. The apparatus according to claim 5, wherein the flow balance element is in an adjustable location with a fixed format.

8. The apparatus according to claim 5, wherein the flow balance element is in an adjustable location and format.

9. The apparatus according to claim 5, wherein the flow balance element is adjustable in size.

10. The apparatus according to claim 1, wherein the flow balance element is in a fixed location and format.

11. The apparatus according to claim 1, further comprising:
means for determining the presence of the first asymmetry in the gas flow pathway, and
means for adjusting the at least one flow balance element.

12. The apparatus according to claim 11, wherein the presence of the first asymmetry is determined by the paramagnetic gas sensor detecting a difference between a measured torque on the test body in the presence of a gas flow and a measured torque on the test body in the absence of a gas flow, and wherein the means for adjusting comprises a control mechanism that is responsive to the detected difference to adjust the at least one flow balance element to reduce the difference.

13. The apparatus according to claim 1, wherein the flow balance element is a protrusion.

14. The apparatus according to claim 1, wherein the flow balance element is an indentation.

15. The apparatus according to claim 1, wherein the flow balance element is a combination of protrusions and indentations.

16. The apparatus according to claim 1, wherein the flow balance element is situated upstream from the test body.

17. The apparatus according to claim 1, wherein the flow balance element is situated do stream from the test body.

18. The apparatus according to claim 1, further comprising a plurality of tow balance elements, where a combination of flow balance elements upstream and/or downstream are used.

19. The apparatus according claim 1, further comprising a plurality of gas inlets that each have external connection points for receiving a measurand gas supply, such that a measurand gas supply can be split upstream of the apparatus and supplied to the plurality of gas inlets at opposite sides of the chamber.

20. The apparatus according to claim 1, further comprising a flow divider within the apparatus to split an incoming gas flow and supply the measurand gas to said positions at opposite sides of the chamber.

21. The apparatus according to claim 20, wherein the flow divider comprises an integrated manifold section.

22. The apparatus according to claim 1, further comprising an optical lever feedback system to maintain the test body in a null position, the optical lever feedback system comprising:
a light source to make a beam of light;
a mirror at the centre of the test body off of which the beam of light reflects;
a pair of photo-detectors to detect a rotation of the test body and provide a photo-electric cell signal; and
a wire coil, attached around the test body that conducts via a suspending wire, wherein the system keeps the test body at a null position by reacting to motion of the test body and amplifying the photo electric cell signal to generate a current in the wire coil that produces a magnetic torque equal and opposite to the perturbing force that would otherwise push the test body away from its null position.

23. The apparatus according to claim 22 farther comprising a meter for measuring the current in the wire coil and for providing a signal output to give an indication of the paramagnetic susceptibility of the gas.

* * * * *

UNITED STATES PATENT AND TRADEMARK OFFICE
CERTIFICATE OF CORRECTION

| | | |
|---|---|---|
| PATENT NO. | : 9,091,658 B2 | Page 1 of 1 |
| APPLICATION NO. | : 13/365814 | |
| DATED | : July 28, 2015 | |
| INVENTOR(S) | : Ian C. Gaskin et al. | |

It is certified that error appears in the above-identified patent and that said Letters Patent is hereby corrected as shown below:

In the Claims

Column 10, line 41 delete "tow" and replace with --flow--.

Signed and Sealed this
Twenty-sixth Day of April, 2016

Michelle K. Lee
*Director of the United States Patent and Trademark Office*